(12) United States Patent
Mark Danieli et al.

(10) Patent No.: US 11,828,740 B2
(45) Date of Patent: Nov. 28, 2023

(54) VOLATILE ORGANIC COMPOUNDS (VOC'S) DIAGNOSIS SYSTEM

(71) Applicant: Early O.M. Ltd., Zur Moshe (IL)

(72) Inventors: Michal Mark Danieli, Zur Moshe (IL); Oron Snir, Nir Galim (IL)

(73) Assignee: EARLY O.M. LTD., Zur Moshe (IL)

( * ) Notice: Subject to any disclaimer, the term of this patent is extended or adjusted under 35 U.S.C. 154(b) by 0 days.

(21) Appl. No.: 17/743,824

(22) Filed: May 13, 2022

(65) Prior Publication Data
US 2023/0062575 A1    Mar. 2, 2023

(30) Foreign Application Priority Data

Aug. 24, 2021  (IL) .......................................... 285830

(51) Int. Cl.
*A01K 1/03* (2006.01)
*G01N 33/00* (2006.01)
(Continued)

(52) U.S. Cl.
CPC ......... *G01N 33/0047* (2013.01); *A01K 1/031* (2013.01); *G01N 33/0001* (2013.01);
(Continued)

(58) Field of Classification Search
CPC ...... A01K 1/031; A01K 15/02; A01K 15/021; A01K 15/029; A61B 5/1105;
(Continued)

(56) References Cited

U.S. PATENT DOCUMENTS

| 4,022,054 A * | 5/1977 | Biederman | ........ G01N 33/0027 116/202 |
| 7,921,810 B2 * | 4/2011 | Lumbroso | .......... A61K 49/0008 119/421 |

(Continued)

FOREIGN PATENT DOCUMENTS

| EP | 1160562 A1 * | 12/2001 | ............. A01K 1/031 |
| EP | 1942342 A1 * | 7/2008 | ............. A01K 15/02 |

(Continued)

OTHER PUBLICATIONS

Ellis Haylee M. et al: Trialing a semi-automated line cage for scent detection by African pouched rats. II , Behavior Analysis: Research and Practice, vol. 19, No. 2, Apr. 12, 2018 (Apr. 12, 2018) , pp. 150-163, XP055948690.
(Continued)

*Primary Examiner* — Ebony E Evans
(74) *Attorney, Agent, or Firm* — BROWDY AND NEIMARK, P.L.L.C.

(57) ABSTRACT

A diagnosis system and method for detecting various Volatile Organic Compounds (VOCs) in a biological sample by utilizing a smart platform configured to harness animal bio-sensors trained to detect various VOC's which may indicate various pathologies, and by conducting various data collection practices and analysis methods in order to produce output results. The diagnosis system and method is configured to analyze behavioral parameters concerning the animal bio-sensor and provide a non-invasive and safe diagnostic solution that does not involve exposing a patient to radiation or any other potentially harmful procedure.

19 Claims, 10 Drawing Sheets

(51) Int. Cl.
*G01N 33/493* (2006.01)
*G01N 35/00* (2006.01)
*G01N 35/02* (2006.01)
*A61B 5/11* (2006.01)
*A61B 5/00* (2006.01)

(52) U.S. Cl.
CPC ..... *G01N 33/493* (2013.01); *G01N 35/00584* (2013.01); *G01N 35/02* (2013.01); *A61B 5/1105* (2013.01); *A61B 5/4011* (2013.01); *G01N 2035/00346* (2013.01)

(58) Field of Classification Search
CPC .. A61B 5/4011; G01N 33/00; G01N 33/0001; G01N 2035/00346
See application file for complete search history.

(56) References Cited

U.S. PATENT DOCUMENTS

| | | | |
|---|---|---|---|
| 8,370,072 B2 | 2/2013 | Fernandez | |
| 9,880,138 B1 * | 1/2018 | Hall | A61B 10/0038 |
| 10,709,108 B2 * | 7/2020 | Nolan | A01K 15/02 |
| 2001/0047771 A1 * | 12/2001 | Bulanda | A01K 15/02 |
| | | | 119/712 |
| 2003/0008407 A1 | 1/2003 | Fu | |
| 2003/0028327 A1 | 2/2003 | Brunner | |
| 2006/0191319 A1 * | 8/2006 | Kurup | G01N 33/0034 |
| | | | 73/23.34 |
| 2006/0236661 A1 | 10/2006 | Kurt | |
| 2012/0077159 A1 | 3/2012 | Araujo | |
| 2012/0131985 A1 * | 5/2012 | Brasfield | G01N 33/0057 |
| | | | 73/23.34 |
| 2016/0282352 A1 | 9/2016 | Martino | |
| 2016/0345539 A1 | 12/2016 | Mark-Danieli | |
| 2017/0000905 A1 * | 1/2017 | Betts-Lacroix | G01N 33/497 |
| 2017/0016906 A1 * | 1/2017 | Hirotsu | G01N 33/57488 |
| 2018/0235178 A1 * | 8/2018 | Sapir | A01K 15/02 |
| 2019/0277823 A1 | 9/2019 | Simon | |
| 2020/0008395 A1 | 1/2020 | Mischley | |
| 2021/0251191 A1 * | 8/2021 | Lee | A01K 15/021 |
| 2022/0095948 A1 * | 3/2022 | Mitchell | A61B 5/097 |

FOREIGN PATENT DOCUMENTS

| | | | | |
|---|---|---|---|---|
| WO | WO-2007057901 A2 * | 5/2007 | | A01K 15/02 |
| WO | 2013/184936 A1 | 12/2013 | | |
| WO | WO-2013184936 A1 * | 12/2013 | | A01K 15/02 |
| WO | 2014106852 A1 | 7/2014 | | |
| WO | WO-2015118524 A1 * | 8/2015 | | A01K 1/031 |
| WO | 2019/115983 A1 | 6/2019 | | |

OTHER PUBLICATIONS

Bauer Pierre et al: "Remote Medical Scent Detection of Cancer and Infectious Diseases With Dogs and Rats: a Systematic Review", Research Square, Jul. 26, 2021 (Jul. 26, 2021), XP055885668.

* cited by examiner

VOLATILE ORGANIC COMPOUNDS (VOC'S) DIAGNOSIS SYSTEM

FIELD OF THE INVENTION

The present invention generally relates to a diagnosis system and method and, more particularly, to a diagnosis system and method for detecting various Volatile Organic Compounds (VOCs) in a biological sample by utilizing a smart platform configured to harness animal bio-sensors trained to detect various VOC's and by conducting various data collection practices and analysis methods in order to produce output results.

BACKGROUND OF THE INVENTION

The importance of early detection/diagnosis of diseases cannot be overstated and bears tremendous implications on the general welfare, life expectancy and a type of medical treatment available for a patient. For example, an early detection/diagnosis of a disease may enable a patient to receive a treatment with lower levels of toxicity, reduce its exposure to radiation and as a result, dramatically improve its chances of survival. In diseases like various types of cancer, current diagnostic methods are limited and do not provide sufficient means to curb the increase of cancer-related deaths.

Nowadays, a cancer type disease such as a lung cancer, is usually detected in its relatively late stages. Such a late diagnosis usually requires aggressive treatment, which impairs the quality of life of a patient and is often less effective. When lung cancer is detected early, surgical intervention can contribute to patient prolonged life expectancy and as a result, a patient diagnosed with an early-stage lung cancer, may expect a significantly longer life expectancy in comparison with a patient diagnosed with a late-stage lung cancer.

Traditional chest X-rays and other traditional diagnostic tests may indicate incorrect negative results and therefore, a cancer type disease may not be detected in its early stages. At the same time, CT scans, which have an ability to detect lesions of one mm in size, tend to produce erroneous positive results, which in turn may contribute to unnecessary surgeries or biopsies.

Another example to a traditional detection technique is mammography scan, used to diagnose breast cancer. Although the fact that mammography reduces the mortality rate and allows treatment with low toxicity, it may detect non-cancerous findings and as a result, some patients are sent for unnecessary further tests, receive unnecessary treatments, and experience unnecessary anxiety. In addition, mammography is less efficient detecting breast cancer in women having dense breast tissue.

Alternative approaches to these traditional diagnostic tools have sought to identify biomarkers using blood samples and chemical analysis. However, these approaches have many disadvantages. In the case of lung cancer patients, when examining biomarkers separately, it turns out that they are not suitable to be used as a diagnostic tool, and it is still unclear which testing system will reach the required level of accuracy and sensitivity.

Detection and identification of diseases through scent may overcome some of these disadvantages. Volatile Organic Compounds (VOCs) such as alkene, methyl-alkene, aromatic compounds such as benzene, etc., have been identified using Gas Chromatography Mass Spectrometry GCMS, which examines chromatography and gas compression in lung cancer patients' exhalation. Wherein the detection is based on the fact that the relative concentrations of these exhaled compounds differentiate between sick and healthy volunteers. However, GCMS testing is unable to detect most exhaled chemicals and therefore may miss most diagnostic markers.

For many decades, organizations/military forces used dogs and other animals, for example rodents such as rats, to detect odor signatures since, to date, there is no instrument that can substitute the nose of a well-trained animal.

Reports of cancer patients being diagnosed using animals bio-sensors first appeared in 1989, then again in 2001 and multiplied over the following years. In addition, some studies have shown that some cancers such as melanoma and bladder cancer may be identified by the odor emanating from biological samples taken from patients.

The use of rats as animal bio-sensors has developed based on the vast knowledge accumulated in various studies indicating their highly developed sense of smell which is expressed in their ability to detect odors in very low concentrations and their further ability to focus on a particular odor from a collection of odors. One particular advantage of using an animal bio-sensor over other systems which are on the market is the fact that an animal bio-sensor is intuitively able to detect an "odor stamp" or "odor image", wherein the technologies developed by humans utilize a complicated procedure of characterizing each molecule that makes up a particular odor.

Over the past few years, there has been a growing interest in the possibility of using human odor signatures as biometric identifiers. A novel approach to provide detection of various VOC's present in biological samples may be achieved by a detection system that utilizes the extremely sensitive abilities of certain animals to detect VOC's and as a result, to provide an indication to a certain biological pathology such as a disease or any other medical condition. For example, it is well recognized that tumors secrete materials into the bloodstream, urine and other body secretions that in turn, may be detected by a diagnostic testing. Apart from various types of cancer, many diseases may also be recognized by the detection of VOC's, such as various degenerative diseases (Parkinson's, Alzheimer's, Huntington's, etc.), various viral or bacterial diseases, etc.

Using human odor signatures as biometric identifiers has been disclosed by several publications, as briefly discussed below.

Patent application publication US20200008395A1 discloses methods for early detection of Parkinson's diseases (PD), by detecting PD-distinct scent using a trained animal (such as a canine). Said method utilizes animals trained to detect volatile compounds in scent emitted from the body or bodily excrement of a test subjects. According to the disclosure of said patent application publication, the trained animal is preferably an animal having superior olfactory capacity such as canine and swine, having an ability to detect the unique and distinctive scents from people with parkinsonism (PwP) and signal such detection to a human handler. Advantageously, these trained animals can be employed to detect in a test subject the presence of PD-distinctive scents even before the test subject shows any motor or other clinical symptoms.

Patent application publication US20030008407A1 discloses non-invasive diagnostic and monitoring system based on odor detection, wherein a set of volatile markers are determined which are characteristic of a particular condition or disease, and supposed to be found in the exhaled breath of a person or odor from other parts of a body of a test subject. According to said patent application publication, these markers are detected in the breath odor or gaseous emanations from the body or entity noninvasively using a volatile substance detector of sufficient sensitivity, such as an artificial olfactory system and the detected marker data is processed in an artificial neural network.

U.S. Pat. Nos. 7,921,810B2 and 4,022,054A disclose a method and apparatus for detecting a substance in a monitored environment, comprising a training phase to train at least one animal capable of detecting the substance and execute an avoidance/attraction reaction, the training phase is conducted by exposing the trained animal to a certain air volume in order to detect specific scents of relatively low concentration entrained in air volume.

Patent application publication US20160345539A1 discloses a system and method for detecting a medical condition in a test subject and comprising training an animal to detect a condition, such as cancer, wherein the training sample is a gaseous sample or vapor generated by a cell population associated with the predetermined condition, and introduced into the animal's enclosure using a syringe. The population of cells associated with the predetermined condition may be, for example, a culture of an established cell line associated with the predetermined condition. Simultaneously with, or subsequent to, presentation of the training sample, the animal is subjected to an adverse stimulus (negative reinforcement), such as an electric shock. The animal is allowed to perform a first predetermined response in order to avoid, escape or terminate the adverse stimulus.

Patent application publication US20180235178A1 discloses a system, method and computer program product for animal based olfactory detection, designated to detect substances in a sequence of filters and includes providing one or more enclosures, each housing an animal, each enclosure including a sample presenting structure via which only a single olfactory sample is presented to the animal at any given time, and generating an output indication of olfactory detection of target substances in the sequence of filters.

Patent application publication WO2014106852A1 discloses a canine biological sensor (a dog) based system for detecting odors emitted from target materials, such as dangerous materials, illegal materials or from the body of a subject (human or animal) that may have diseases (such as cancer) and providing automatic alerts regarding any change in the functionality of sensors upon detecting a predefined target odor.

Although the publications disclosed above relate to the field of substances' detection systems, none of said publications teach, alone or in combination, a volatile organic compounds (VOCs) diagnosis system that utilizes animal bio-sensors to detect various biological samples in order to detect various pathologies, wherein said VOCs diagnosis system utilizes designated conveying and alternatively sealed exposure means, by analyzing behavioral parameters concerning the animal bio-sensor.

There is a need to provide a VOCs based detection & diagnosis system that takes advantage of using human odor signatures as biometric identifiers by uniquely detected markers shed as a result of a certain medical condition and deposited in a biological sample and thus, providing an early indication of possible medical condition. Furthermore, such a detection/diagnosis system may provide a non-invasive and safe diagnostic method that does not involve exposing a patient to radiation or any other potentially harmful procedure.

SUMMARY OF THE INVENTION

The following embodiments and aspects thereof are described and illustrated in conjunction with systems, devices and methods which are meant to be exemplary and illustrative and not limiting in scope. In various embodiments, one or more of the above-described problems have been reduced or eliminated, while other embodiments are directed to other advantages or improvements.

According to one aspect, there is provided a volatile organic compounds (VOCs) diagnosis system, comprising: at least one animal bio-sensor, at least one animal-machine enclosure (AME) configured to accommodate and provide detection means in order to monitor the animal bio-sensor, at least one alternatively sealed exposure means configured to interduce to at least one animal bio-sensor, VOCs emitted from at least one biological sample collected from a patient, at least one conveying means configured to convey the at least one exposure means, and at least one controller, wherein the at least one animal bio-sensor is trained to react differently to various VOCs present within said biological sample; and wherein the at least one controller is configured to analyze, in accordance with data collected from said detection means, the reaction of said at least one animal bio-sensor upon exposure to a certain biological sample and produce an output indicating findings related to said biological sample.

According to some embodiments, the AME comprises: an enclosure configured to accommodate the at least one animal bio-sensor, and at least one detection means, wherein the detection means further enabling an autonomous inspection of various behavioral parameters exhibited by the animal bio-sensor upon an exposure to a biological sample.

According to some embodiments, the at least one exposure means comprises: an outer receptacle comprising an interaction component configured to enable the introduction of VOCs into an AME, and an inner receptacle configured to be accommodated within the outer receptacle and store the biological sample, wherein the exposure means is configured to interact with an AME and wherein the inner receptacle is configured to alternately expose the biological sample stored within to the inner volume of the outer receptacle.

According to some embodiments, the alternate exposure of the biological sample is conducted using a spring load mechanism.

According to some embodiments, the alternate exposure of the biological sample is conducted using an electric motor.

According to some embodiments, the alternate exposure of the biological sample is conducted using an electromagnetic mechanism.

According to some embodiments, the air volume within the outer receptacle is configured to be replaced between each interaction with an AME.

According to some embodiments, the exposure means further comprises a heating mechanism configured to raise the temperature of VOCs designated to be introduced into an AME.

According to some embodiments, the heating mechanism is configured to operate while the exposure means is not currently interacting with an AME.

According to some embodiments, the exposure means is configured to be detachably attached to the conveying means.

According to some embodiments, the exposure means is configured to provide autonomous exposure to various VOCs present within the biological sample.

According to some embodiments, the conveying means is configured to operate in an autonomous manner.

According to some embodiments, the conveying means is a conveyor configured to convey multiple exposure means.

According to some embodiments, the system further comprising a device configured to read data related to each biological sample.

According to some embodiments, the detection means are various sensors.

According to some embodiments, wherein the exposure to the various VOCs present within the biological sample is conducted by allowing the animal bio-sensor to sniff the said sample.

According to some embodiments, the AME further comprises various signaling means configured to provide the animal bio-sensor with indications regarding various events.

According to some embodiments, the AME further comprises a feedback mechanism configured to provide positive/negative reinforcements to the animal bio-sensor.

According to some embodiments, the at least one animal bio-sensor is a trained rat or imprinted rat.

According to some embodiments, the output indicating medical test findings is an analysis of the reaction of multiple animal bio-sensors that have been exposed to the biological sample.

According to some embodiments, the at least one biological sample collected from a patient is a urine sample.

According to some embodiments, the animal bio-sensor is trained to detect VOCs related to various diseases such as various cancer types, various degenerative diseases, various bacterial diseases, various viral diseases, etc.

According to some embodiments, a detection of a disease-related VOCs triggers a predictable and detectible behavior of the animal bio-sensor.

According to some embodiments, at least one controller is a programmable logic controller (PLC).

According to some embodiments, at least one controller is configured to run a Laboratory Information Management System (LIMS).

According to some embodiments, at least one controller is configured to utilize a machine learning model in order to provide an improved output indicating medical test findings.

According to some embodiments, at least one controller is configured to utilize big data analysis in order to extract valuable data from a large pool of gathered data.

According to some embodiments, at least one controller is configured to utilize both an embedded software and/or a cloud computing platform in order to monitor the general operation of the system, conduct an analysis of the behavior of said at least one animal bio-sensor and produce an output indicating medical test findings.

According to some embodiments, the animal bio-sensor is designated to undergo an olfactory imprinting exposure to certain VOCs during both pregnancy and infancy.

According to second aspect, there is provided a method for using VOCs detection system comprising the steps of: receiving a biological sample collected from a patient, processing the biological sample using conveying means configured to interduce the biological sample to at least one animal-machine enclosure (AME) comprising detection means and accommodated by at least one animal bio-sensor, exposing the animal bio-sensor to the biological sample by using exposure means, analyzing, in accordance with said detection means, the reaction of said at least one animal bio-sensor, and producing an output indicating test findings.

According to some embodiments, the animal bio-sensor is trained to stay a longer time period in proximity to a positive biological sample and a shorter time period in proximity to a negative biological sample.

According to some embodiments, the animal bio-sensor is trained to stay $0<t<6$ seconds in proximity to a negative biological sample and $6<t<12$ seconds in proximity to a positive biological sample.

According to some embodiments, the air volume within the AME is configured to be replaced after each biological sample detection cycle.

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention.

In the Figures.

DETAILED DESCRIPTION OF SOME EMBODIMENTS

Figure 1A:
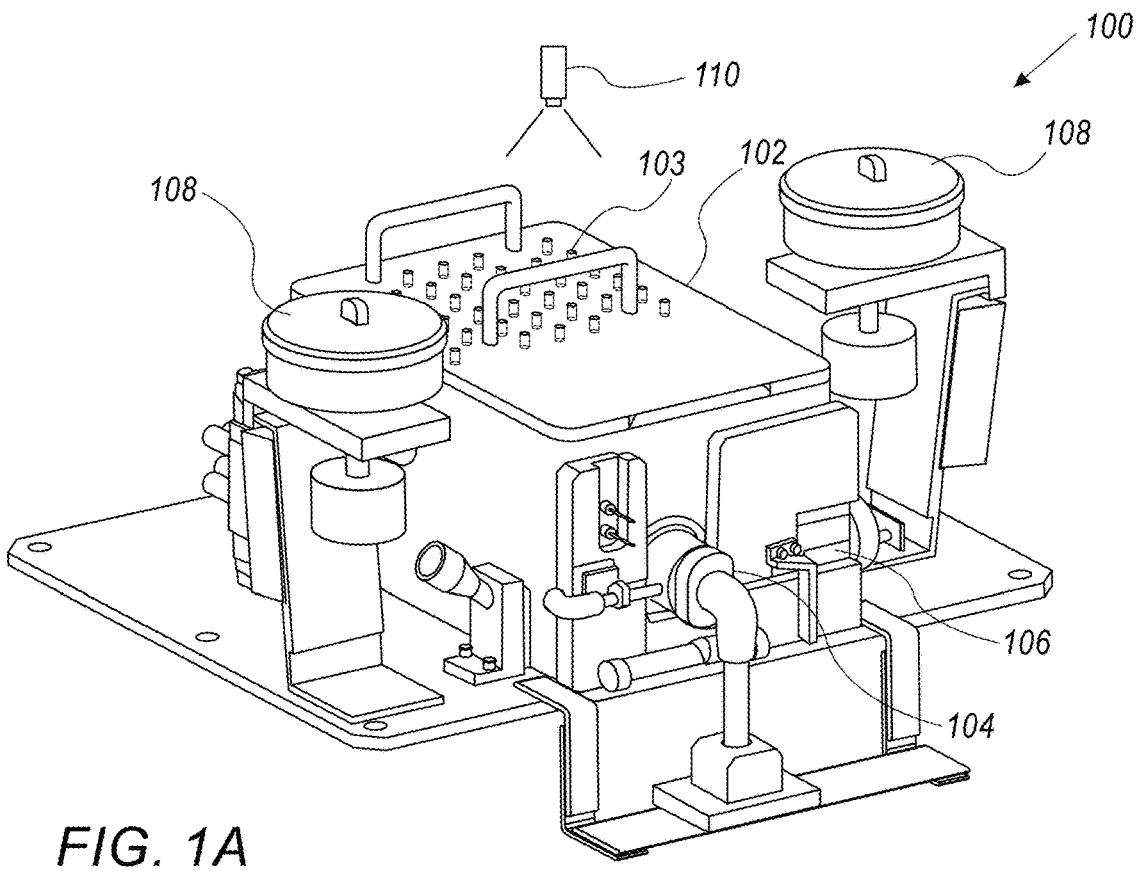
FIGS. 1A & 1B constitute schematic perspective views of an animal-machine enclosure (AME) of a VOCs diagnosis system, according to some embodiments of the invention.

In the following detailed description, numerous specific details are set forth in order to provide a thorough understanding of the invention. However, it will be understood by those skilled in the art that the present invention may be practiced without these specific details. In other instances, well-known methods, procedures, and components, modules, units and/or circuits have not been described in detail so as not to obscure the invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "controlling" "processing," "computing," "calculating," "determining," "establishing", "analyzing", "checking", "setting", "receiving", or the like, may refer to operation(s) and/or process(es) of a controller, a computer, a computing platform, a computing system, a cloud computing system or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes.

Unless explicitly stated, the method embodiments described herein are not constrained to a particular order or sequence. Additionally, some of the described method embodiments or elements thereof can occur or be performed simultaneously, at the same point in time, or concurrently.

The term "Controller", as used herein, refers to any type of computing platform or component that may be provisioned with a Central Processing Unit (CPU) or microprocessors, and may be provisioned with several input/output (I/O) ports, for example, a general-purpose computer such as a personal computer, laptop, tablet, mobile cellular phone, controller chip, SoC or a cloud computing system.

The term "Odor signature" as used herein, refers to an odor that may be composed from a complexed variety of molecules that may react together and/or have a specific combination of molecules in its three-dimensional structure. Each disease has its own and unique odor signature. Animals can detect an odor signature at low PPT (parts per trillion) concentration, which represents a high sensitivity compared with other technologies. For example, artificial assays are designed to identify specific molecules that may be present at very low concentrations where the artificial assays are not sensitive enough to detect. On the contrary, animal bio-sensors such as rats may recognize an odor signature, which may be still unknown to other detection assays.

The present invention discloses a system and method for an early diagnosis of various VOCs present within a biological sample. According to some embodiments, the VOCs diagnostic system may comprise an animal-machine enclosure (AME) configured to accommodate at least one animal bio-sensor that may be a rodent such as a rat.

According to some embodiments, the AME may comprise detection means configured to monitor the animal bio-sensor. According to some embodiments, the VOCs diagnosis system may comprise conveying means configured to convey at least one exposure means to a designated position, in order to enable interaction between said exposure means and the AME and hence, introducing VOCs emanating from a biological sample collected from a patient to the animal bio-sensor. According to some embodiments, a controller may be configured to control the operation and/or detection/diagnosis/analysis/presentation of results associated with the operation of the VOCs diagnosis system.

According to some embodiments, the animal bio-sensor may be trained to react differently to various VOCs present within said biological sample, the detection means may detect the reaction of the animal bio-sensor and the controller may be configured to analyze, in accordance with data collected from said detection means, the reaction of the animal bio-sensor and produce output indicating findings related to said biological sample. According to some embodiments, the controller may be further configured to control the general operation of the VOCs diagnosis system.

According to some embodiments, said output generated by the VOCs diagnosis system may be medical test findings related to a certain medical condition. For example, any pathology that has an influence upon the concentration and/or composition of VOCs present within a biological sample may be detected and diagnosed by using the VOCs diagnosis system as disclosed above.

According to some embodiments, each animal bio-sensor may work individually in an isolated AME, in order for it not to be influenced by herd effect and avoid any possible inter-influence between animal bio-sensors. According to some embodiments, positive reinforcement may be used as a training method to encourage detection abilities of animal bio-sensors.

According to some embodiments, an animal bio-sensor training protocol may include a regulated exposure of the animal bio-sensor to various odors of interest. Such an exposure may be followed or conducted simultaneously with a positive reinforcements regime in order to encourage the animal bio-sensor to perform distinctive behavioral act/s detectable by the VOCs diagnosis system. According to some embodiments, the regulated exposure of the animal bio-sensor may be conducted through its mother, while the animal bio sensor is still an embryo/fetus.

According to some embodiments, the training protocol is based on the general operation flow of the VOCs diagnosis system. For example, first the biological sample reaches a designated area. Second, the animal bio-sensor smells and accordingly identifies specific/general odor, whether the biological sample is a positive or a negative sample. Third, the VOCs diagnosis system automatically analyzes the results that were collected from the at least one animal bio-sensor.

According to some embodiments, Genetic imprinting or Olfactory-based imprinting may be used to enhance detection abilities among an animal bio-sensor by influencing sniffing behavior. According to some embodiments, a genetic imprint may be based on exposing young rats to various diseases, for example, imprinting may be based on exposing young rats to various cancer types that may be detected by their unique VOCs emanating from a biological sample (such as urine, saliva, blood, etc.) collected from a cancer patient.

According to some embodiments, an unborn rat may be exposed to the targeted odor of various diseases such as various cancer type cells during its embryonic development through exposing its mother to said targeted odor. As a result, the offspring (F1 generation) will be born with an olfactory sensitivity to said particular odor. According to some embodiments, individuals from F1 exhibiting an enhanced ability to detect the targeted odor will be inbred and exposed again to the same targeted odor.

According to some embodiments, the VOCs diagnosis system may be operated in a fully autonomous manner, enabling an automated manipulation and detection of biological samples as well as an automated production of positive/negative results to be analyzed and stored in a database.

According to some embodiments, various Machine Learning (ML) technics may be applied to analyzes and/or operate the detection/diagnosis process conducted by the VOCs diagnosis system. For example, a sequence algorithm which may be an internal statistical ML model that may be used for monitoring the animal bio-sensors and increase output accuracy. According to some embodiments, an ML model may start collecting data once an animal bio-sensor first accommodates to the AME itself, and may be used to analyze and collect data during the first training period, in order to determine a "score level" indicating the animal bio-sensor accuracy.

According to some embodiments, various statistical analysis methods may be used to analyzes and/or operate the detection/diagnosis process conducted by the VOCs diagnosis system. For example, descriptive statistics such as ICC (Intraclass Correlation Coefficient) may be utilized during the training process of each animal bio-sensor in order to determine the performance score achieved by said animal bio-sensor.

According to some embodiments, in accordance with the results of various statistical analysis methods, a certain percentage of the animal bio-sensors may be defined as unqualified and will not participate in upcoming performance evaluations. For example, and according to some embodiments, a qualified animal bio-sensor should be able to reach a detection level of at least 90% (true positive) and an error level of up to 10% (false positive).

According to some embodiments, after a succession of a training period, and before an animal bio-sensor starts participating in an actual detection session, a session of screening may be conducted that may include using a sequence of a known biological samples acting as calibration sequences to be assessed by the animal bio-sensor. A group of several animal bio-sensors, (for example, rats) may assess biological samples exposed by exposure means designated to deliver VOCs emanating from each biological sample.

According to some embodiments, each animal bio-sensor may then get an individual opportunity to sniff each biological sample. According to some embodiments, each animal bio-sensor is then detected by the detection means and the results are analyzed via the controller which is designated to produce a final indication of +/−(positive/negative result) for each biological sample. According to some embodiments, the final output is a combination of all animal bio-sensor individuals that took part in the calibration process. The above procedure may be conducted several times until the results are satisfying, i.e., exhibit a high correlation with the actual composition of the calibration sequence. According to some embodiments, the same process described above may be used to detect VOCs in an actual detection cycle.

Figure 1B:
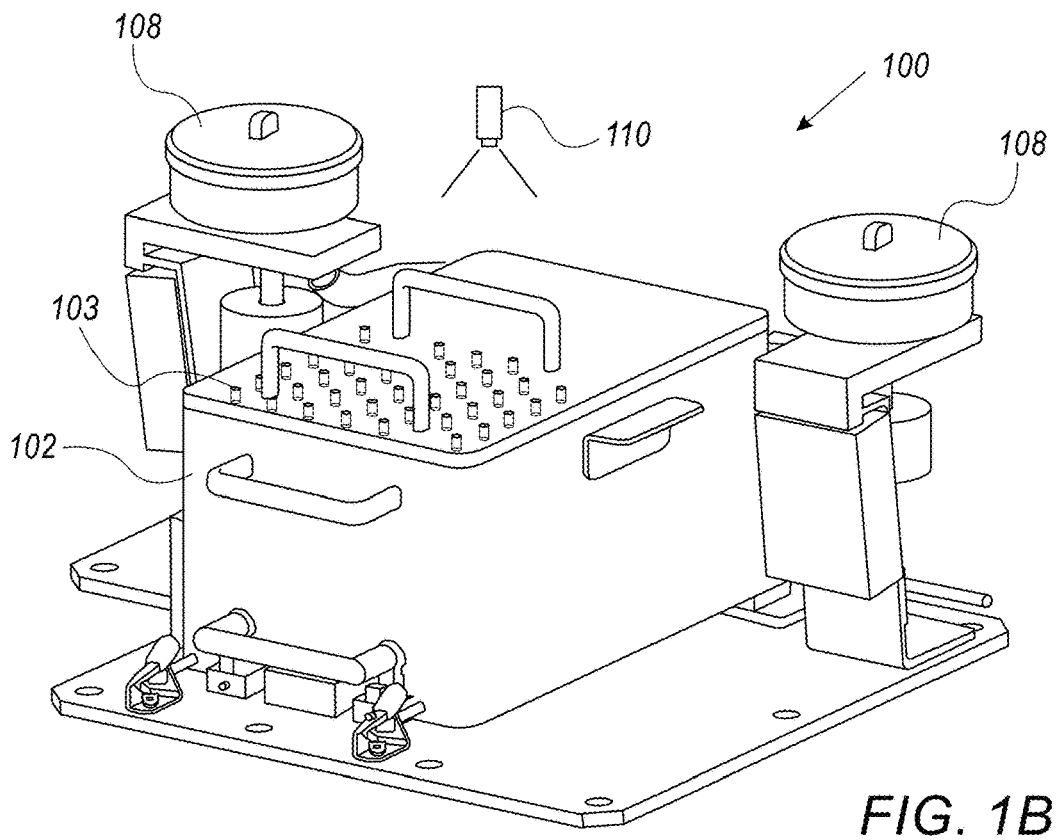
Figures 2A, 2B, 2C, 2D:
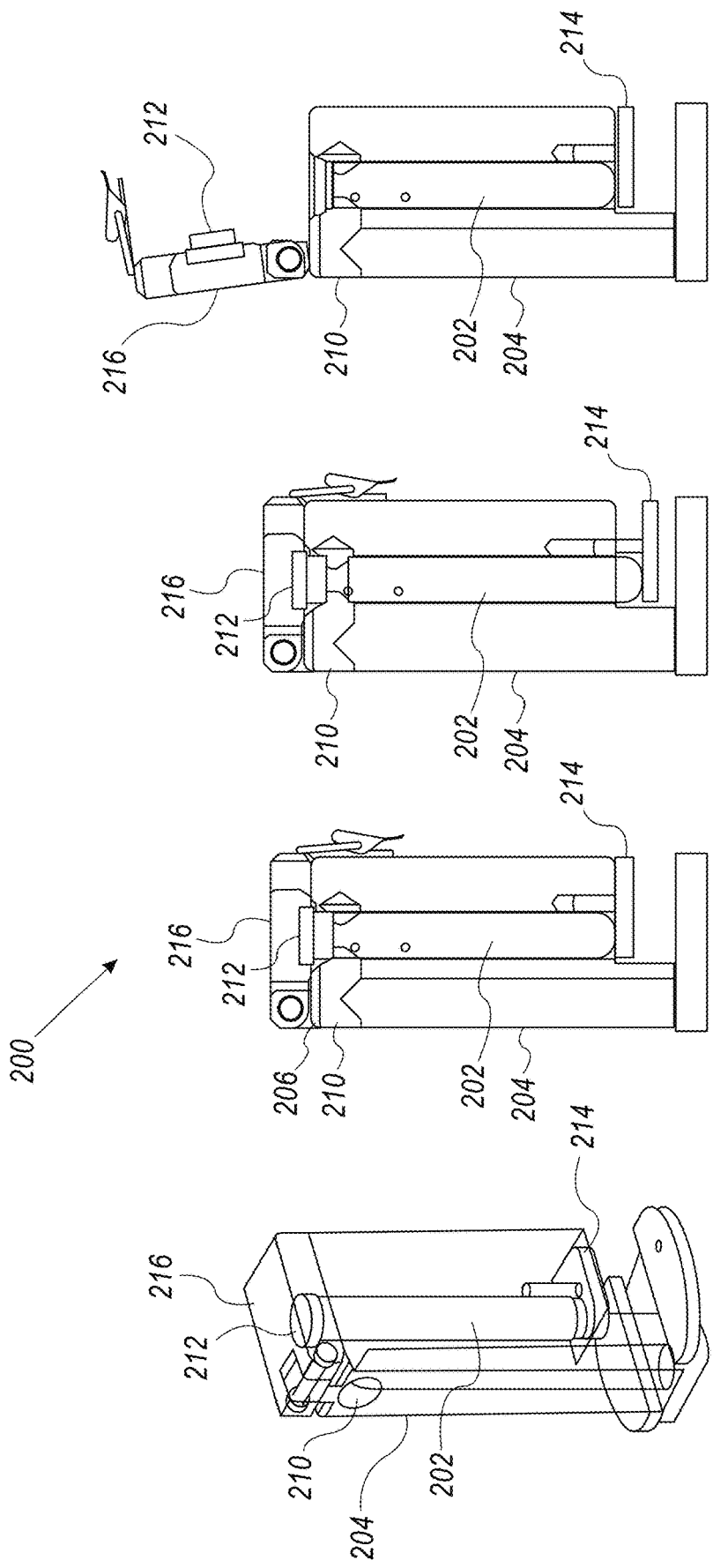
FIGS. 2A-2D constitute schematic perspective views of an exposure means of a VOCs diagnosis system, according to some embodiments of the invention.

Reference is now made to FIG. 1A & FIG. 1B which schematically illustrate an animal-machine enclosure (AME) 100 of a VOCs diagnosis system 10. As shown, AME 100 may comprise a cage compartment 102 configured to accommodate an animal bio-sensor. According to some embodiments, cage compartment 102 is designed to provide sufficient space to the animal bio-sensor designated to perform inside. Cage compartment 102 may further comprise ventilation means such as ventilation apertures 103, etc.

According to some embodiments, AME 100 may comprise an exposure port 104 that may be for example, a sniffing shaft configured to interduce VOCs emanating from a biological sample. According to some embodiments, exposure port 104 may further comprise a barrier 106 configured to be alternately closed/open. According to some embodiments, said barrier 106 may be any electric/hydraulic/mechanic/magnetic driven barrier configured to be opened/closed to allow a predesignated time window for the animal bio-sensor to sniff VOCs emanating from a biological sample.

According to some embodiments, AME 100 may further comprise at least one feeding device 108 configured to provide the animal bio-sensor with sufficient quantity of food during its stay within cage compartment 102. According to some embodiments, the quantity of food available to the animal bio-sensor during its stay within cage compartment 102 is calculated in advance in order to ensure that the animal bio-sensor will be performing in an ideal way. According to some embodiments, a particular food/water regime may also be used as a reinforcement reward encouraging an animal bio-sensor to work. For example, an animal bio-sensor may be rewarded with food/water after each detection cycle, etc.

According to some embodiments, various detection means 110 are configured to operate in proximity to cage compartment 102 or, alternatively, be embedded within AME 100 in order to monitor the animal bio-sensor. Detection means 110 may enable an autonomous inspection of various behavioral parameters exhibited by the animal bio-sensor upon an exposure to VOCs emanating from a biological sample. For example, a trained rat may be exposed, through exposure port 104, to certain VOCs emanating from a urine sample, the rat may then sniff said VOCs during a certain time frame while being constantly monitored by detection means 110.

According to some embodiments, detection means 110 may be a motion, vibration or an IR sensor or a visual camera, a microphone or any other known sensing device. According to some embodiments, the data collected by detection means 110 may be sent to a controller (not shown) for further analysis.

According to some embodiments, exposure to certain VOCs emanating from a biological sample may trigger a predictable behavior exhibited by the animal bio-sensor and detectable by detection means 110. For example, detection means 110 may be a visual camera or any type of sensor, configured to monitor some area of the AME 100 in order to provide a comprehensive monitoring of the animal bio-sensor as it moves within its inner space, hence, detection means 110 may provide an ability to detect behavioral characteristics before and after said exposure to VOCs emanating from a biological sample.

According to some embodiments, detection means 110 may be a visual camera or any type of sensor configured to monitor the area around or within exposure port 104 and/or barrier 106 in order to monitor an animal bio-sensor while it sniffs the VOCs emanating from the biological sample.

Reference is now made to FIGS. 2A-2D which schematically illustrate exposure means 200 of a VOCs diagnosis system 10. As shown, exposure means 200 may be configured to interduce to at least one animal bio-sensor VOCs emanating from at least one biological sample collected from a patient.

According to some embodiments, an inner receptacle 202, that may be adapted with plug 212, is configured to store a biological sample and further configured to be accommodated within an outer receptacle 204. According to some embodiments, inner receptacle 202 is configured to alternately expose the biological sample stored within, to the inner volume of void 210 using various mechanisms. According to some embodiments, a designated mechanism is configured to expose the inner volume of inner receptacle 202 to the inner volume of void 210 such that, when exposure means 200 is in a designated position with regard to AME 100, VOCs emanating from the biological sample may be translocated through void 210, through exposure port 104 and into the AME 100, enabling an animal bio-sensor to be exposed to said VOCs.

According to some embodiments, void 210 and exposure port 104 share similar dimensions and are configured to allow close contact with each other such that VOCs emanating from the biological sample may be translocated through void 210, through exposure port 104 and into the AME 100 without leakage of outside contamination, thus enabling an animal bio-sensor to be exposed to said VOCs.

According to some embodiments, inner receptacle 202 may be a test tube adapted with a plug 212. According to some embodiments, an actuator (not shown) may be configured to cause the opening of plug 212 and expose the inner volume of inner receptacle 202 to the inner volume of void 210. According to some embodiments, the actuator may be configured to cause a separation of inner receptacle 202 from plug 212. According to some embodiments, inner receptacle 202 may be configured to be based on a platform 214 configured to be manipulated by the actuator and as a consequence, to enable close/open positions of inner receptacle 202 or an alternate thereof.

According to some embodiments, the mechanism configured to manipulate inner receptacle 212/the actuator/platform 214, may be any known moving mechanism, such as a mechanical mechanism, an electrical mechanism, a hydraulic mechanism, a magnetic mechanism, etc. According to some embodiments, cover 216 may be configured to alternatively seal outer receptacle 204 and provide an access for an insertion of inner receptacle 202.

According to some embodiments, the air within inner receptacle 202 and/or outer receptacle 204 and/or AME 100 is designated to be replaced between each exposure cycle in order to avoid contamination and provide each animal bio-sensor in each AME 100 with the same VOCs concentration and composition. According to some embodiments, the biological sample stored within inner receptacle 202 is designated to be heated before/between each exposure cycle in order to enhance emanation of VOCs.

Figure 3A:
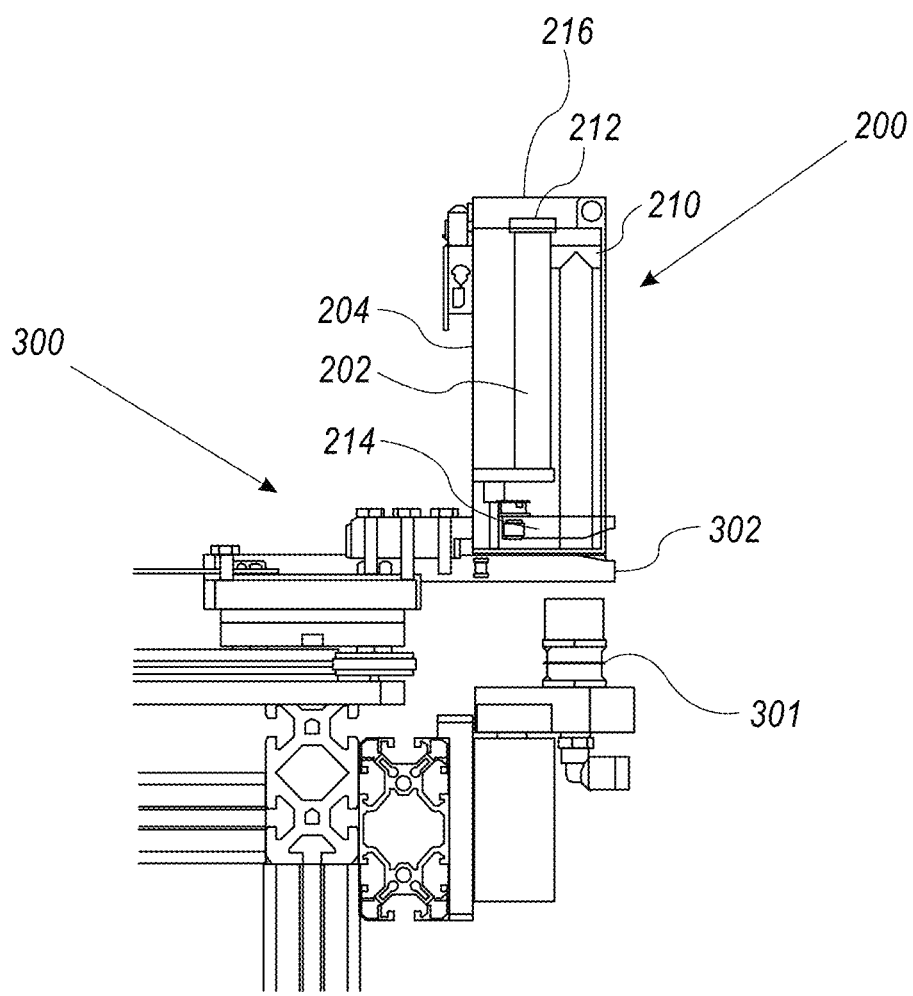
FIGS. 3A-3C constitute schematic perspective views an AME, exposure means and conveying means of a VOCs diagnosis system, according to some embodiment of the invention.
Figure 3B:
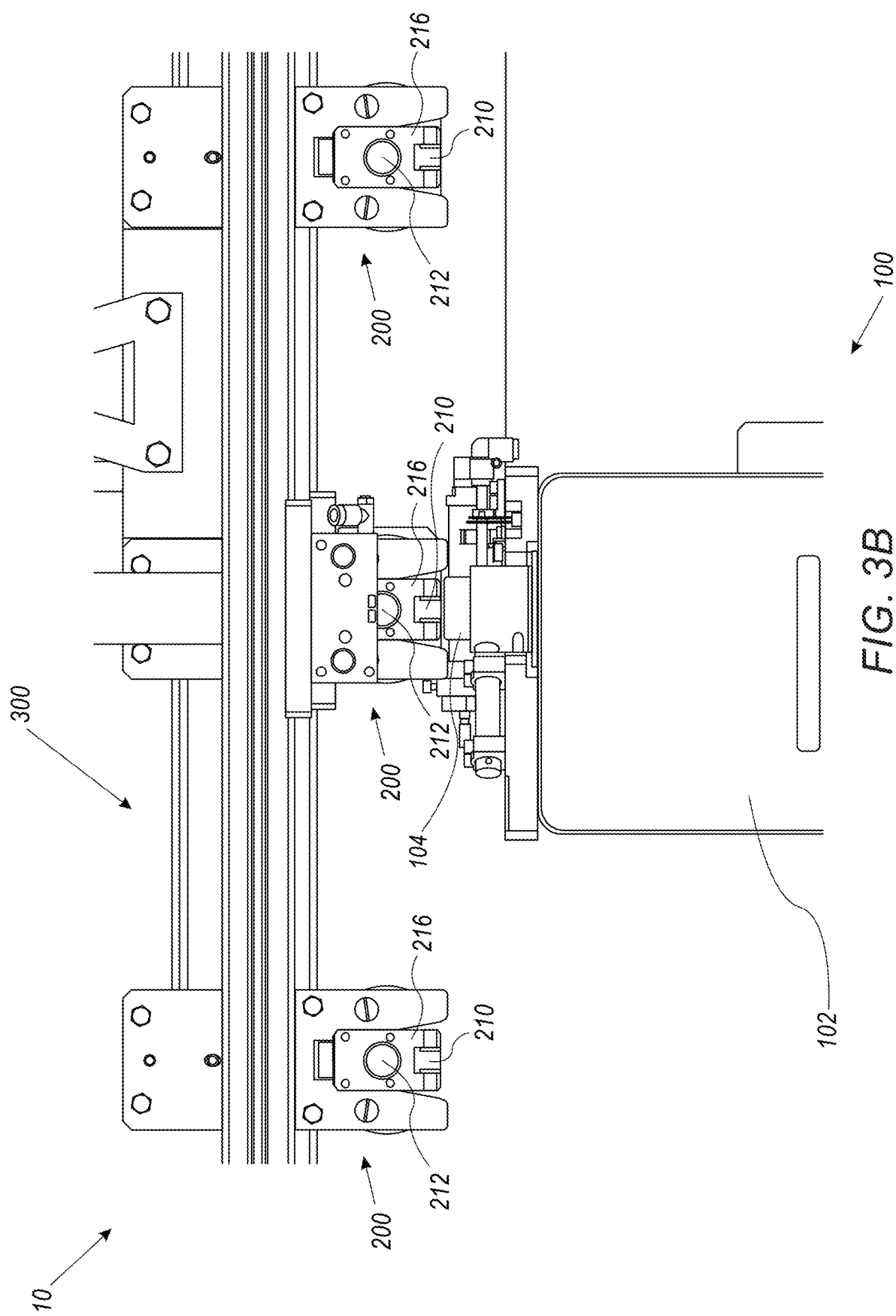
Figure 3C:
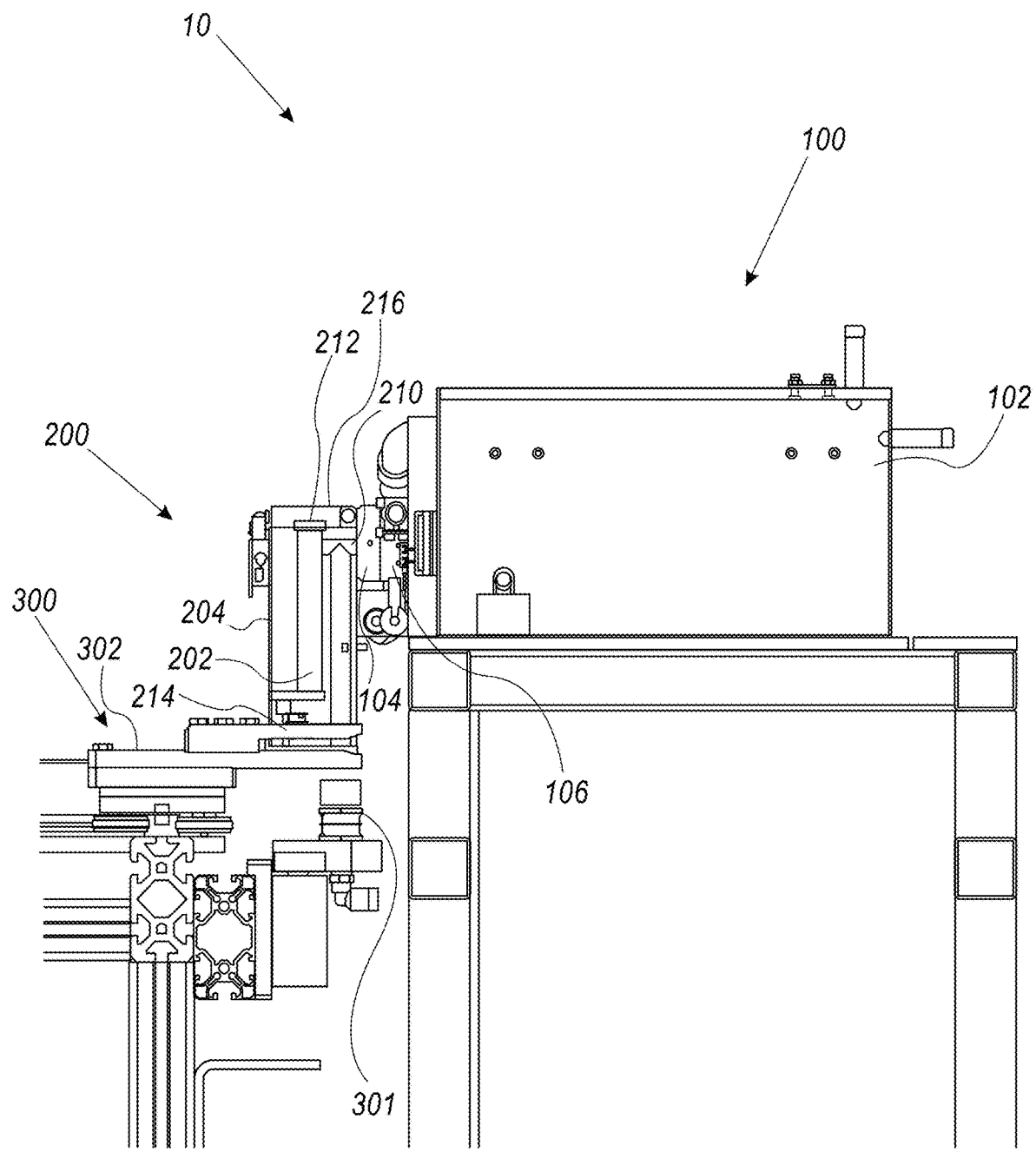

Reference is now made to FIGS. 3A-3C which schematically illustrate an interaction between an AME 100, exposure means 200 and conveying means 300 of a VOCs diagnosis system 10. As shown, conveying means 300 may be configured to convey exposure means 200 to a designated position in order to enable interaction between said exposure means 200 and the AME 100 and hence, introduce VOCs emanating from a biological sample collected from a patient and stored within exposure means 200, to an animal bio-sensor.

According to some embodiments, a controller (not shown) may be configured to control the operation and/or detection/diagnosis/analysis/presentation of results associated with the operation of the VOCs diagnosis system 10. According to some embodiments, conveying means 300 may be a traditional conveyor system configured to convey exposure means 200 along a designated path. According to some embodiments, conveying means 300 may be further equipped with fixture means 302, each designated to carry at least one exposure means 200.

According to some embodiments, conveying means 300 is configured to convey exposure means 200 to a designated position that is approximately in front of AME 100, such that void 210 is located approximately in front of exposure port 104 of AME 100 and a communication may be made. According to some embodiments, upon arriving to said designated position and establishing a contact, barrier 106 may be alternately closed/open to allow VOCs to emanate from a biological sample stored in exposure means 200, through void 210, through exposure port 104 and reach the animal bio-sensor within AME 100.

According to some embodiments, upon arriving to said designated position, detection means 110 (such as a motion or IR sensor/a camera, microphone, etc.) embedded within/located in close proximity to cage compartment 102, may monitor the animal bio-sensor's behavior before/while/after being exposed to said VOCs. For example, detection means 110 may enable an autonomous inspection of various behavioral parameters exhibited by the animal bio-sensor (for example, a trained rat) upon exposure to VOCs emanating from a biological sample.

According to some embodiments, the animal bio-sensor may sniff said VOCs during a certain time frame while being constantly monitored by detection means 110, and the data collected by the detection means 110 may then be sent to a controller (not shown) for further analysis. According to some embodiments, exposure to certain VOCs emanating from a certain biological sample should trigger a predictable behavior of the animal bio-sensor that may be detected by detection means 110.

According to some embodiments, VOCs diagnosis system 10 may also be equipped with an air replacement mechanism 301 which may be any type of air manipulation device such as a vacuum pump, a fan, etc. designated to withdraw/eject air from/into exposure means 200 in order to replace its contained air and hence, avoiding a contaminated exposure. For example, air replacement mechanism 301 may be configured to be connected to exposure means 200 and may be configured to create vacuum within outer receptacle 204 between exposure cycles and/or sample exchanges.

According to some embodiments, after the end of an exposure cycle and/or exchanging a sample to be assessed, the air replacement mechanism 301 may stop and allow fresh air to enter outer receptacle 204, hence preventing contaminated air from affecting the next exposure cycle of the next sample to be assessed. According to some embodiments, said process may also be conducted by air ejected into outer receptacle 204 in order to force out any contaminated air. According to some embodiments, the air replacement mechanism 301 may be configured to alternatively communicate with exposure means 200 by using any known communicating port/joint, etc.

According to some embodiments, air replacement mechanism 301 may be configured to withdraw/eject air from/into AME 100 by utilizing the components and operations disclosed above and in order to replace the air contained within AME 100 and hence, avoid contaminated air that may affect the animal bio-sensor assessing the next sample.

Figure 4A:
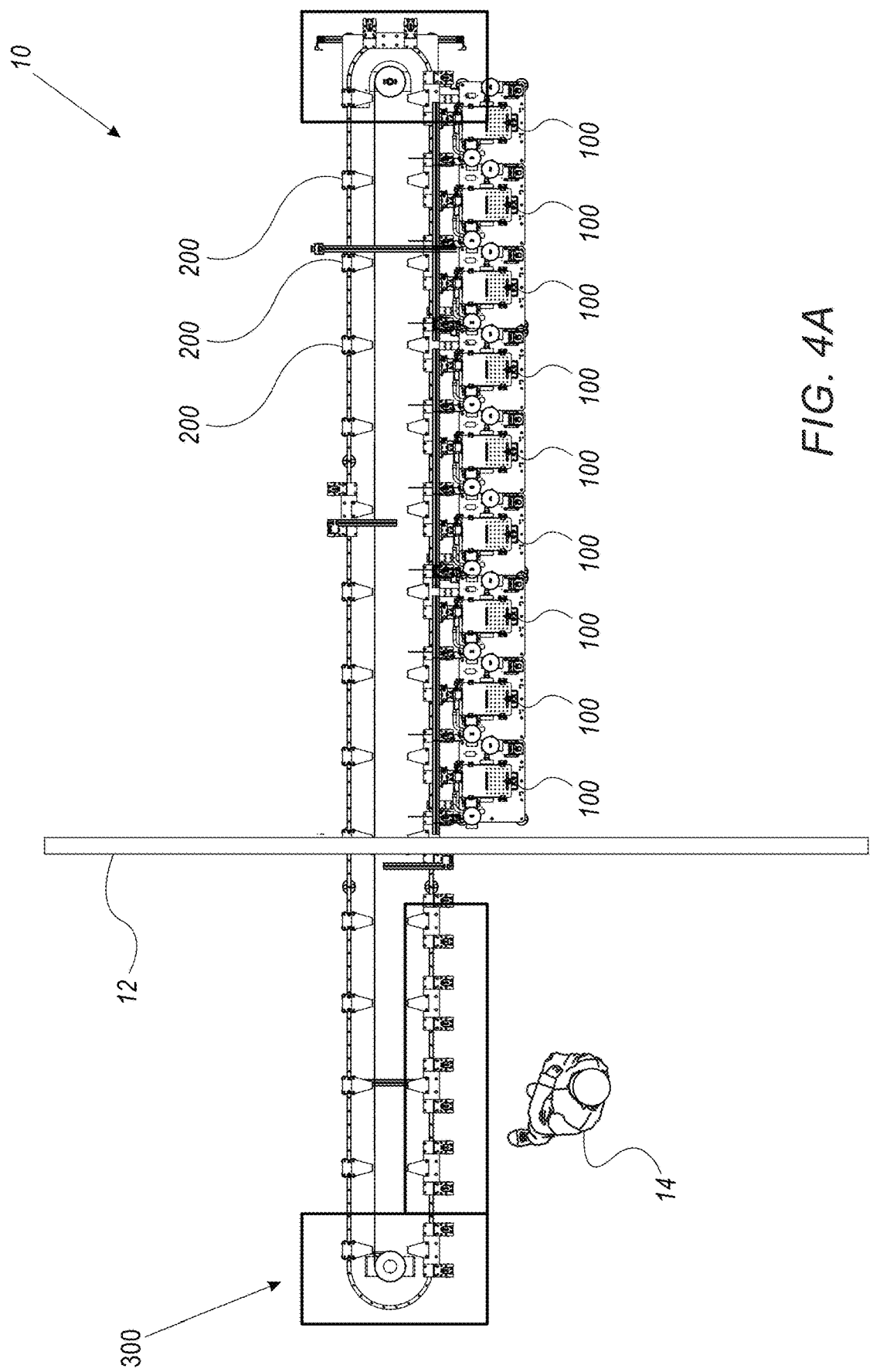
FIGS. 4A-4C constitute schematic top and perspective views of a VOCs diagnosis system, according to some embodiment of the invention.
Figure 4B:
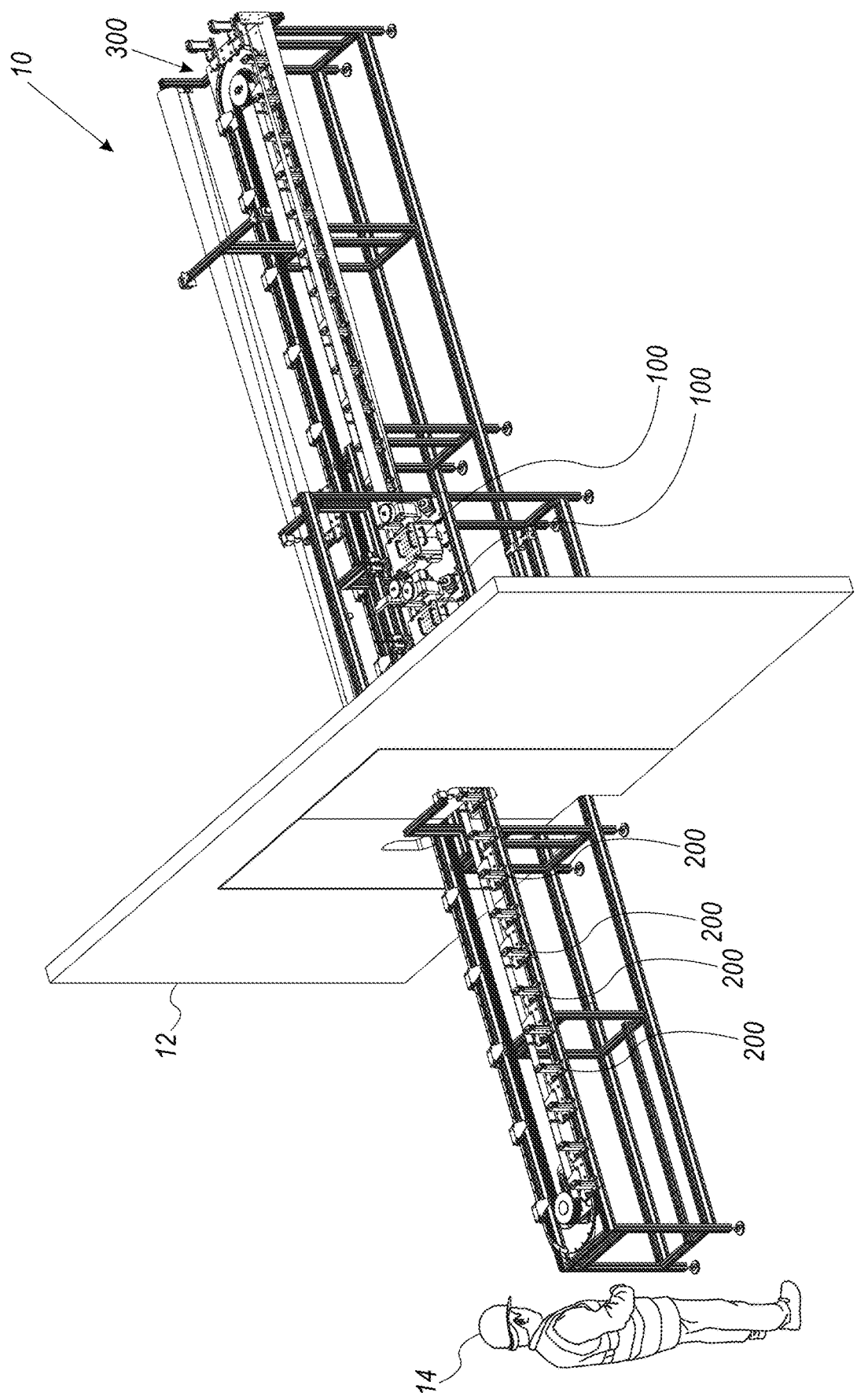
Figure 4C:
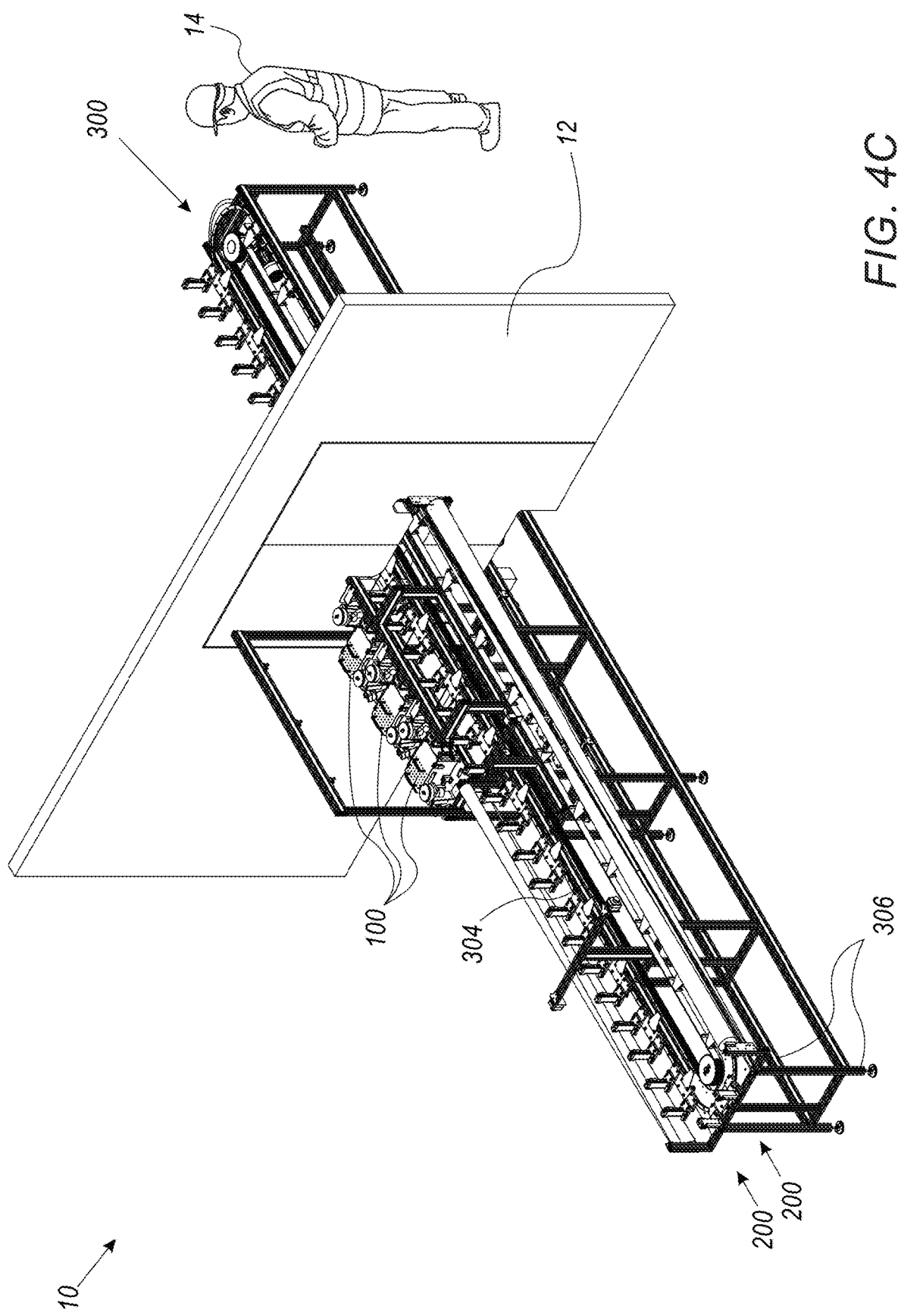

Reference is now made to FIGS. 4A-4C which schematically illustrate top and perspective views of a VOCs diagnosis system 10. As shown, conveying means 300 may comprise of conveyor belt 304 configured to be attached to multiple fixture 302 (shown in FIGS. 3A & 3C) that in turn, is configured to hold exposure means 200. According to some embodiments, the framework configured to support the VOCs diagnosis system 10 may further comprise noise (that may be caused by vibrations, etc.) reduction mechanism 306 in order to provide the animal bio-sensor a quiet surrounding that does not interfere or affect its detection abilities.

According to some embodiments, conveying means 300 is configured to convey multiple exposure means 200 to a designated position with regard to AME 100 such that VOCs emanating from the biological sample may be translocated through void 210, through exposure port 104 and into the AME 100, enabling an animal bio-sensor to be exposed to said VOCs as shown in the figures. According to some embodiments, each exposure means 200 may be designated to interact with each of a multiple AMEs 100.

According to some embodiments and as previously disclosed, the air within inner receptacle 202 and/or outer receptacle 204 and/or AME 100 is designated to be replaced between each exposure cycle in order to avoid contamination and provide each animal bio-sensor in each AME 100 with the same VOCs concentration and composition. According to some embodiments, the biological sample stored within inner receptacle 202 is designated to be heated before/between each exposure cycle in order to enhance emanation of VOCs.

According to some embodiments, VOCs diagnosis system 10 may be partly operated by an operator 14 and/or operator 14 may be in charge of manipulating various components of VOCs diagnosis system 10. For example, operator 14 may be in charge of pairing inner receptacles 202 with outer receptacles 204 in accordance with desired diagnostic procedure purposes. Operator 14 may also be in charge of conveyor means 300 by determining the pace of introducing exposure means to the animal bio-sensors, hence, operator 14 may have control over the detection process in accordance with professional standards and lab protocols. According to some embodiments, operator 14 may be in charge of the general welfare of animal bio-sensors. For example, operator 14 may be in charge of feeding the animal bio-sensors, transferring and removing animal bio sensors from and into designated AMEs 100, etc.

According to some embodiments, VOCs diagnosis system 10 may further comprise partition 12 that may be either transparent or opaque and configured to provide separation between operator 14 and AME 100. According to some embodiments, said separation may be necessary to reduce possible disturbances caused by the presence of operator 14 that may influence an animal bio-sensor behavior and detection abilities.

According to some embodiments, the manual operation and/or manipulation disclosed above may be conducted in an autonomous manner bay utilizing designated robotic infrastructure to control the overall operations of VOCs diagnosis system 10.

Figure 5A:
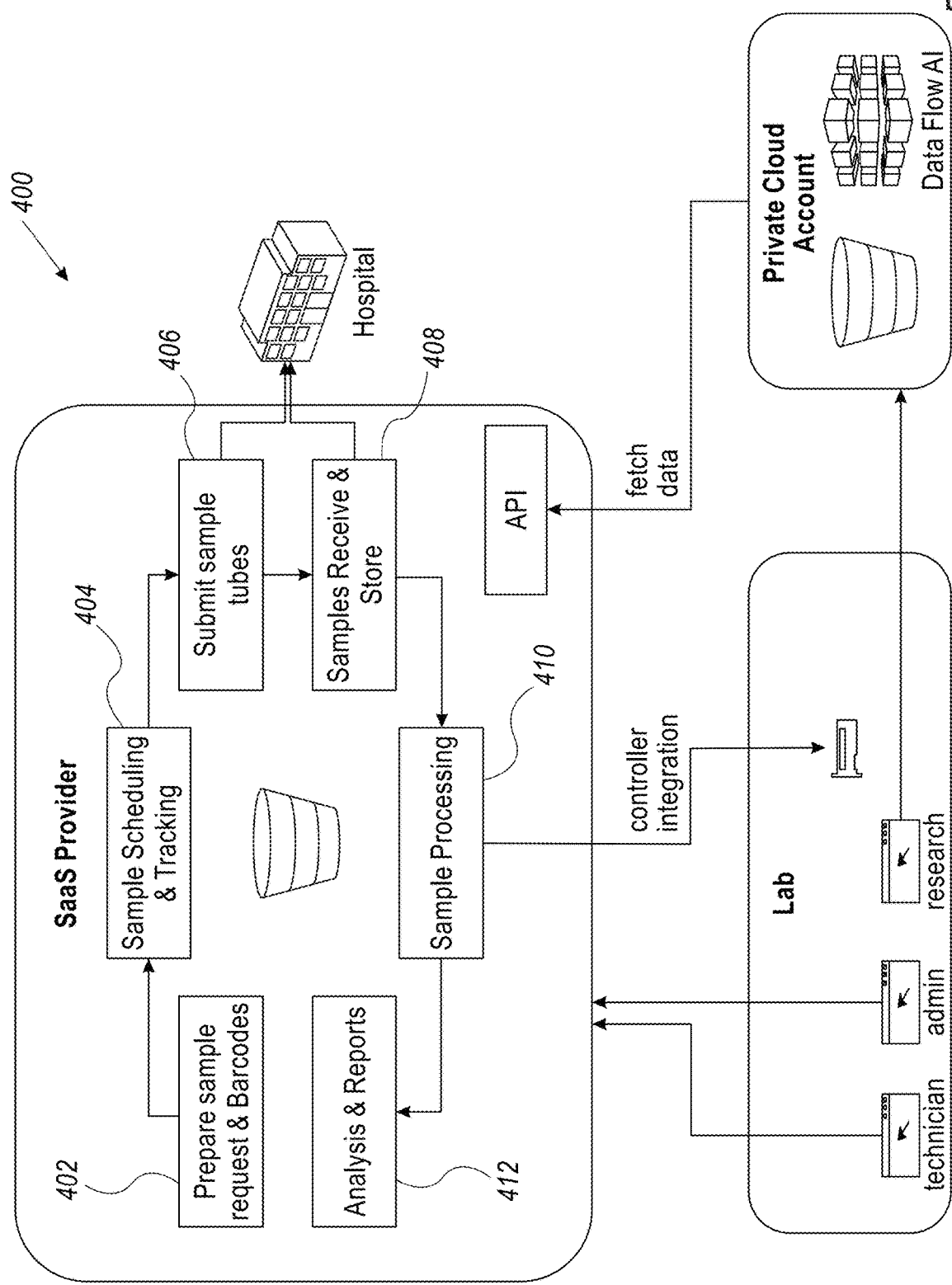
FIG. 5A constitutes a possible operation flow chart describing various operations of a VOCs diagnosis system, according to some embodiment of the invention.

Reference is now made to FIG. 5A which illustrates a possible operation flow chart of a VOCs diagnosis system 10. As shown, cloud 400 (that may be a Software as a Service SaaS provider, etc.) may describe an internal flow of VOCs diagnosis system 10 associated with detection/diagnosis/analysis/presentation of results, etc.

According to some embodiments, in operation 402 the biological sample (that may be sampled in a laboratory) is prepared in accordance with a particular request by a patient, medical Doc, a hospital, a health maintenance (HMO) organization, etc. The biological sample may then be marked by a unique machine-readable format such as a barcode, enabling recognition of said sample along the diagnosis procedure. According to some embodiments, the laboratory sampling the biological samples may have a data integration with cloud 400.

In operations 404 and 406, a biological sample may be tracked using a unique machine-readable format attached to each sample, it may then be submitted for analysis by a patient, medical Doc, a hospital, a health maintenance (HMO) organization, the patient himself/herself, etc.

In operation 408, the submitted biological sample is received and stored in a designated location according to appropriate storing conditions protocol. According to some embodiments, the biological sample may be stored within inner receptacle 202 as disclosed above. For example, the biological sample may be stored within inner receptacle 202 during work or practice sessions.

In operation 410, said biological sample may be processed, exposed to a biological bio-sensor, which in turn may be detected by detection means 110 in order to monitor its behavioral parameters as disclosed above.

In operation 412, the detection results may be collected and then analyzed by a controller incorporated in cloud 400 and an output indicating findings may be produced. For example, after exposing an animal bio-sensor (such as a rat) to VOCs emanating from a biological sample (such as a urine sample), a test result/s report indicating possible pathologies may be issued. According to some embodiments, said controller may be any known type of computing platform or component that may be provisioned with a Central Processing Unit (CPU), for example, controller may be a programmable logic controller (PLC) configured to run various management software/cloud computing applications such as laboratory information management system (LIMS), etc.

According to some embodiment, controlling operation regarding the VOCs diagnosis system 10 may be conducted by a certain controller and the analysis of the collected data may be conducted by another controller. For example, data collection may be conducted by a PLC physically located in close proximity to the VOCs diagnosis system 10, (for example, a PLC may be located in an AI data flow stored on another cloud account) and the analysis of said data may be conducted by a separate controller that may be any type of computing platform such as a cloud computing-based platform, etc., and may use any analysis type such as big-data analysis, algorithmic analysis, ML analysis, LIMS analysis, etc.

Figure 5B:
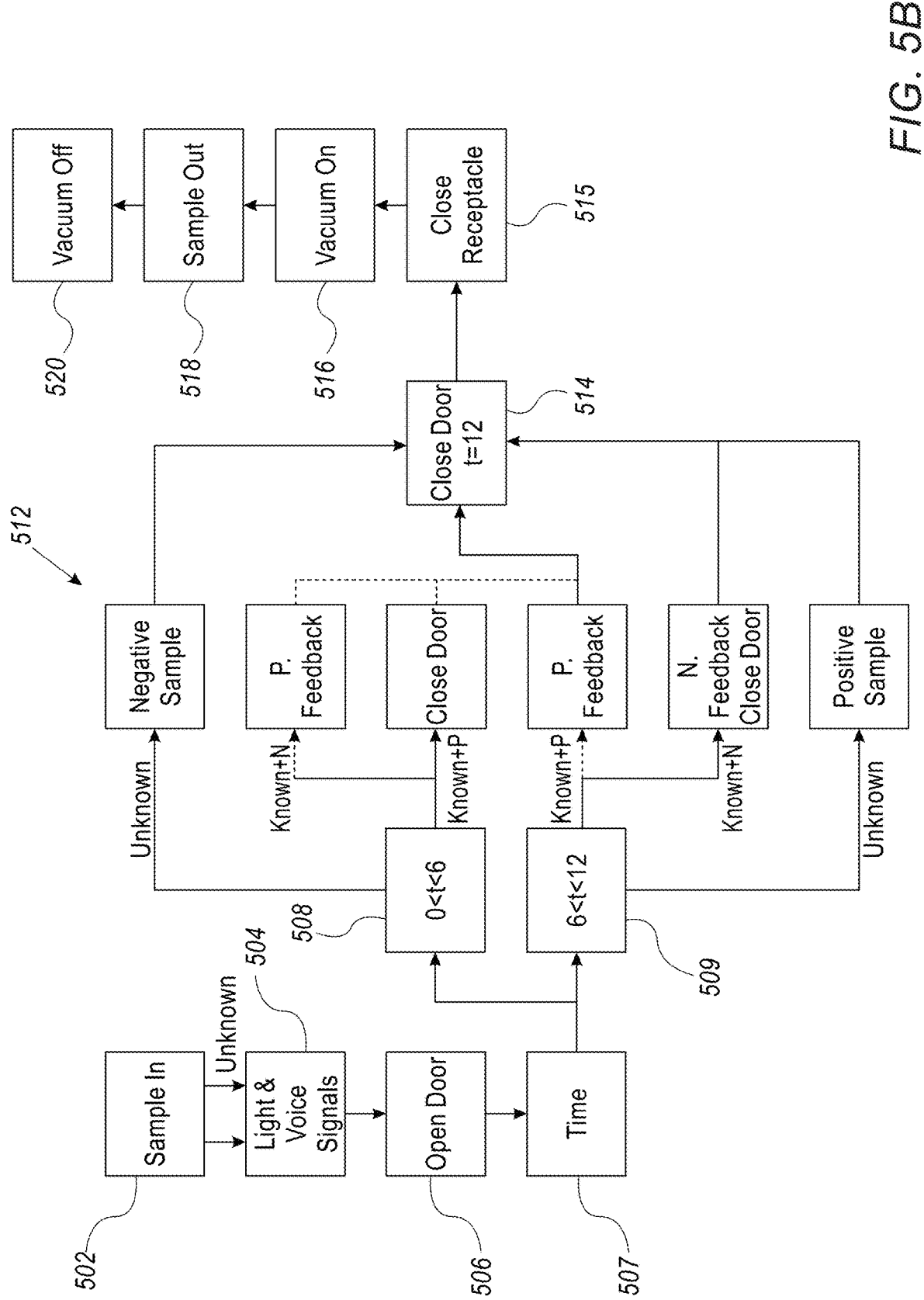
FIG. 5B constitutes a block diagram describing possible operation flow configured to control various operations of a VOCs diagnosis system, according to some embodiment of the invention.

Reference is now made to FIG. 5B which illustrates a block diagram describing possible flow operations configured to control various operations of a VOCs diagnosis system 10.

As previously disclosed, the animal bio-sensor may be trained to react differently to various VOCs present within a biological sample, detection means 110 may detect the reaction of the animal bio-sensor and said controller is configured to analyze, in accordance with data collected from said detection means 110, the behavioral parameters of the animal bio-sensor and produce an output indicating findings related to said biological sample.

As shown, in operation 502 a biological sample may be exposed to an animal bio-sensor as disclosed above. According to some embodiments, the biological sample may be a known sample (for example a calibration or a training sample), wherein exposure to VOCs emanating from said known sample is configured to induce a designated behavior exhibited by the animal bio-sensor. According to some embodiments, various needs/preferences may determine if the known sample may or may not induce a feedback response. For example, a known sample identified correctly by the animal bio-sensor, may induce a positive reinforcement feedback such as food or water or may induce a signal feedback (such as light or voice, etc.). According to some embodiments, said feedback may be either a positive or a negative feedback, (for example, a reward, an unpleasant sound, etc.)

In operation 504, the bio-sensor may be exposed to a sample to be assessed, said exposure to VOCs emanating from said sample may be accompanied by a visual or a vocal signal such as certain lights pattern/color or a designated sound indicating an exposed biological sample to be examined. According to some embodiments, said visual or vocal signal associated with the exposed biological sample may contribute to the working efficiency/accuracy of the animal bio-sensor by clearly marking a new scent to be examined. According to some embodiments, the Animal bio-sensor may undergo a visual or vocal signal-related conditioning to enhance detection abilities or influencing sniffing behavior upon exposure to said conditioning trigger.

As disclosed above and according to some embodiments, conveying means 300 is configured to convey exposure means 200 to a designated position in front of or in close proximity to an AME 100, such that void 210 is located in front of or in close proximity to exposure port 104 of AME 100. In operation 506, upon the arrival of exposure means 200 to said designated position, barrier 106 may be alternately closed/open to allow VOCs to emanate from void 210, through exposure port 104 and inside AME 100 accommodated by the animal bio-sensor.

In operation 507, the animal bio-sensor may then sniff the VOCs emanating from the biological sample for a certain period of time. As disclosed above, detection means 110 are configured to monitor the animal bio-sensor and measure, inter alia, the time it has been actively sniffing said VOCs or other behavioral parameters exhibited.

According to some embodiments, in operation 508 an animal bio-sensor may sniff the VOCs for a shorter time period in comparison with a predetermined threshold (for example, a time period of 0<t<6), as a consequence, the biological sample may be marked as a negative sample by the VOCs diagnosis system 10, wherein a negative biological sample may indicate a patient with no pathological finding.

According to some embodiments, in operation 509 an animal bio-sensor may sniff the VOCs for a longer time period in comparison with a predetermined threshold (for example, a time period of 6<t<12), as a consequence, the biological sample may be marked as a positive sample by the VOCs diagnosis system 10, wherein a positive biological sample may indicate a patient with a possible pathological finding.

According to some embodiments and as disclosed above, in the various operations such as those specified in squares that form the column marked as 512, the response of the animal bio-sensor may be assessed. For example, in case the animal bio-sensor has been exposed to VOCs emanating from an unknown sample, wherein the sniffing or any other behavioral parameter was conducted during a shorter time period in comparison with a predetermined threshold (for example, a time period of 0<t<6), the sample will be identified as negative.

In an opposite example, the animal bio sensor has been exposed to VOCs emanating from an unknown sample, wherein the sniffing or any other behavioral parameter was conducted during a longer time period in comparison with a predetermined threshold (for example, a time period of 6<t<12), the sample will be identified as positive.

According to some embodiments, when the animal bio sensor has been exposed to VOCs emanating from a known sample (for example, a calibration or training sample), a correct identification may lead to different results. For example, a correct identification of a negative/positive sample may result in a positive feedback, and alternatively, false identification of a negative/positive sample may result in a negative feedback.

In operations 514/515 after a predetermined time (for example, more than 12 seconds, etc.) provided for sniffing, barrier 106/outer receptacle 204/inner receptacle 202/exposure port 104 may be closed in order to stop the emanation of VOCSs to the AME 100.

In operation 516 the air within outer receptacle 204/AME 100 may be replaced by utilizing air replacement mechanism 301 (shown in FIGS. 3A and 3C) in order to avoid contamination and provide each animal bio-sensor in each AME 100 with the same VOCs concentration and composition in every exposure cycle. According to some embodiments, after air has been replaced the exposure means 200 may be conveyed by the conveying means 300 to be exposed to another AME 100 or be further treated in any desired way.

In operations 518 and 520, as part of ending an exposure cycle, the inner receptacle 202 may be replaced with another inner receptacle 202 containing another biological sample to be examined. According to some embodiments said replacement may be conducted autonomously or by a human operator 14. According to some embodiments, after the replacement of inner receptacle 202, the air replacement mechanism may be switched off, resulting in an uncontaminated exposure means 200 ready to be exposed to next animal bio sensor.

According to some embodiments, the biological sample stored within inner receptacle 202 may be designated to undergo temperature changes before, between or during each exposure cycle in order to enhance emanation of VOCs. For example, the biological sample stored within inner receptacle 202 may be pre-heated or pre-cooled before an exposure cycle by a designated temperature change element, and may also undergo temperature changes while being conveyed between different AMEs 100 to be assessed. According to some embodiments, applying temperature changes upon the biological sample stored within inner receptacle 202 may be conducted by a temperature change element embedded within inner receptacle 202, or, alternatively, mounted on conveying means 300. According to some embodiments, a designated temperature change chamber may be configured to store at least one inner receptacle 202 and provide pre-heating or pre-cooling before each exposure cycle.

Although the present invention has been described with reference to specific embodiments, this description is not meant to be construed in a limited sense. Various modifications of the disclosed embodiments, as well as alternative embodiments of the invention will become apparent to persons skilled in the art upon reference to the description of the invention. It is, therefore, contemplated that the appended claims will cover such modifications that fall within the scope of the invention.

The invention claimed is:

1. A volatile organic compounds (VOCs) medical diagnosis system, comprising:
   (i) at least one animal bio-sensor,
   (ii) at least one animal-machine enclosure (AME) configured to accommodate the animal bio-sensor,
   (iii) at least one alternatively sealed exposure means configured to introduce to at least one animal bio-sensor, VOCs emitted from at least one solid or liquid or gas biological sample collected from a patient,
   (iv) at least one detection means configured to collect data regarding the behavioral characteristics of the animal bio sensor upon exposure to the VOCs,
   (v) at least one conveying means configured to convey the at least one exposure means, and
   (vi) at least one controller,
   wherein the at least one animal bio-sensor is trained to react differently to various VOCs present within said biological sample; and
   wherein the at least one controller is configured to analyze, in accordance with data collected from said detection means, the reaction of said at least one animal bio-sensor upon exposure to a certain biological sample and produce an output indicating findings related to said biological sample.

2. The system of claim 1, wherein the AME comprises:
   (i) an enclosure configured to accommodate the at least one animal bio-sensor, and
   (ii) at least one detection means, wherein the detection means further enabling an autonomous inspection of various behavioral parameters exhibited by the animal bio-sensor upon an exposure to a biological sample.

3. The system of claim 1, wherein each exposure means comprises:
   (i) an outer receptacle comprising an interaction component configured to enable the introduction of VOCs into one of the at least one AME, and
   (ii) an inner receptacle configured to be accommodated within the outer receptacle and store the biological sample,
   wherein the exposure means is configured to interact with an AME and wherein the inner receptacle is configured to alternately expose the biological sample stored within to the inner volume of the outer receptacle.

4. The system of claim 3, wherein the exposure means further comprises a temperature change mechanism configured to change the temperature of VOCs designated to be introduced into an AME.

5. The system of claim 1, wherein the AME further comprises various signaling means configured to provide the animal bio-sensor with indications regarding various events.

6. The system of claim 1, wherein the output is designated to specify medical test findings which comprise an analysis of the reaction of multiple animal bio-sensors that have been exposed to the biological sample.

7. The system of claim 1, wherein the at least one biological sample collected from a patient is a urine sample.

8. The system of claim 1, wherein the animal bio-sensor is trained to detect VOCs related to various diseases.

9. The system of claim 8, wherein a detection of a disease-related VOCs triggers a predictable and detectible behavior of the animal bio-sensor.

10. The system of claim 1, wherein the at least one controller is a programmable logic controller (PLC).

11. The system of claim 1, wherein the at least one controller is configured to run a Laboratory Information Management System (LIMS).

12. The system of claim 1, wherein the at least one controller is configured to utilize a machine learning model in order to provide an improved output indicating medical test findings.

13. The system of claim 1, wherein the at least one controller is configured to utilize big data analysis in order to extract valuable data from a large pool of gathered data.

14. The system of claim 1, wherein the at least one controller is configured to utilize both an embedded software and a cloud computing platform in order to monitor the general operation of the system, conduct an analysis of the behavior of said at least one animal bio-sensor and produce an output indicating medical test findings.

15. The system of claim 1, wherein the animal bio-sensor is designated to undergo an olfactory imprinting exposure to certain VOCs during both pregnancy and infancy.

16. A method for using VOCs medical diagnosis system comprising the steps of:
   (i) receiving at least one solid or liquid or gas biological sample collected from a patient,
   (ii) utilizing at least one conveying means configured to convey at least one alternatively sealed exposure means,
   (iii) exposing at least one an animal bio-sensor to the at least one biological sample using the exposure means by introducing VOCs emitted from the at least one biological sample to the at least one animal bio-sensor designated to accommodate an animal-machine enclosure (AME),
   (iv) utilizing at least one detection means configured to collect data regarding the behavioral characteristics of the at least one animal bio sensor upon exposure to the VOCs during a diagnostic session, wherein said animal bio-sensor has been trained using positive reinforcement means,
   (v) using a controller to analyze, in accordance with data collected from the detection means, the reaction of the at least one animal bio-sensor upon exposure to a certain VOCs emitted from the at least one biological sample, and
   (vi) producing an output indicating medical test findings related to said biological sample.

17. The method of claim 16, wherein the animal bio-sensor is trained to stay a longer time period in proximity to a positive biological sample and a shorter time period in proximity to a negative biological sample.

18. The method of claim 16, wherein the animal bio-sensor is trained to stay $0<t<6$ seconds in proximity to a negative biological sample and $6<t<12$ seconds in proximity to a positive biological sample.

19. The method of claim 16, wherein each AME holds a certain air volume which is designated to be replaced after each biological sample detection cycle.

* * * * *